(12) United States Patent
Glufke et al.

(10) Patent No.: US 6,689,918 B2
(45) Date of Patent: Feb. 10, 2004

(54) METHOD FOR PRODUCING DICARBONYL COMPOUNDS

(75) Inventors: Uta Glufke, Basel (CH); Paul Hanselmann, Brig-Glis Schweiz (CH)

(73) Assignee: Lonza AG, Basel (CH)

( * ) Notice: Subject to any disclaimer, the term of this patent is extended or adjusted under 35 U.S.C. 154(b) by 0 days.

(21) Appl. No.: 10/275,982

(22) PCT Filed: May 18, 2001

(86) PCT No.: PCT/EP01/05739
§ 371 (c)(1), (2), (4) Date: Nov. 19, 2002

(87) PCT Pub. No.: WO01/90036
PCT Pub. Date: Nov. 29, 2001

(65) Prior Publication Data
US 2003/0171622 A1 Sep. 11, 2003

(30) Foreign Application Priority Data
May 19, 2000 (EP) .............................................. 00110670

(51) Int. Cl.$^7$ .............................................. C07C 45/40
(52) U.S. Cl. ........................ 568/388; 568/389; 568/398
(58) Field of Search ................................ 568/388, 389, 568/398

(56) References Cited

U.S. PATENT DOCUMENTS

| | | | |
|---|---|---|---|
| 3,153,066 A | 10/1964 | Weber | 260/586 |
| 5,831,130 A | 11/1998 | Miller et al. | 568/397 |

OTHER PUBLICATIONS

International Search Report from applicants' corresponding PCT application.
Karl Griesbaum et al., Chem. Ber., (1991), 124(4), 947–56.
Karl Griesbaum et al., Chem. Ber., (1998), 121(10), 1795–9.

*Primary Examiner*—Johann Richter
*Assistant Examiner*—Sikarl A. Witherspoon
(74) *Attorney, Agent, or Firm*—Fisher, Christen & Sabol

(57) ABSTRACT

A method for producing α-dicarbonyl compounds of formula (I):

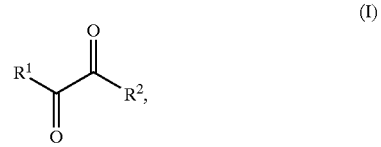

wherein $R^1$ and $R^2$, independently of each other, mean $C_{1-6}$-alkyl. In the method, an α,β-unsaturated ketone of formula (II):

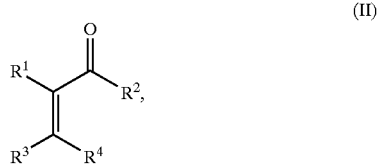

wherein $R^1$ and $R^2$ have the meaning above and $R^3$ and $R^4$, independently of each other, mean hydrogen, $C_{1-6}$-alkyl or di-$C_{1-6}$-alkylamino, is reacted with ozone in the absence of a catalyst and the resultant ozonide is treated reductively.

4 Claims, No Drawings

METHOD FOR PRODUCING DICARBONYL COMPOUNDS

This is a national stage application of International Patent Application No. PCT/EP01/05739, filed on May 18, 2001, that has priority benefit of European Patent Application No. 00110670.7, filed on May 19, 2000.

The invention relates to a process for the preparation of α-dicarbonyl compounds (α-diketones), in particular for the preparation of 2,3-pentanedione.

2,3-Pentanedione is a constituent of the butter aroma and is therefore prepared industrially as a synthetic aroma substance. It is suitable—like other α-dicarbonyl compounds—also as a synthesis building block for the preparation of further fine chemicals and active ingredients.

2,3-Pentanedione can be prepared, for example, by condensation of lactic acid (2-hydroxypropanoic acid) (U.S. Pat. No. 5,831,130). The condensation reaction is carried out at temperatures of about 300° C.

U.S. Pat. No. 3,153,066 describes the ozonolysis of ketones in the presence of selenium dioxide for the preparation of α-dicarbonyl compounds.

It was an object of the present invention to provide a simple process for the preparation of α-dicarbonyl compounds.

It has been found that α-dicarbonyl compounds can be obtained by reacting α,β-unsaturated ketones with ozone.

The invention thus relates to a process for the preparation of α-dicarbonyl compounds of the formula

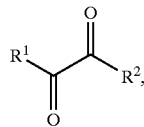

I in which $R^1$ and $R^2$, independently of one another, are $C_{1-6}$-alkyl. The process is characterized in that an α,β-unsaturated ketone of the formula

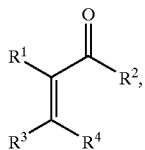

II in which $R^1$ and $R^2$ have the meaning given above, and $R^3$ and $R^4$, independently of one another, are hydrogen, $C_{1-6}$-alkyl or di-$C_{1-6}$-alkylamino, is reacted with ozone, and the reaction mixture is then worked-up reductively.

"$C_{1-6}$-Alkyl" is to be understood here and in the text below as meaning all linear or branched alkyl groups having 1–6 carbon atoms, such as, for example, methyl, ethyl, propyl, isopropyl, butyl, isobutyl, sec-butyl, tert-butyl, pentyl, isopentyl, tert-pentyl, neopentyl, hexyl or isohexyl.

The radical $R^1$ is preferably methyl. The radical $R^2$ is preferably ethyl.

The reaction with ozone advantageously takes place in a suitable solvent at temperatures in the range from −100° C. to 30° C. Suitable solvents are, for example: alcohols, such as, for example, methanol, ethanol, propanol, isopropanol, butanol, pentanol or hexanol; organic acids, such as, for example, acetic acid or customary inert solvents, such as, for example, hexane, dichloromethane, ethyl acetate. It is, however, also possible to use mixtures of the above solvents. Particular preference is given to methanol or a mixture of methanol and dichloromethane.

An ozone-containing stream of gas, such as, for example, an air/ozone mixture or an oxygen/ozone mixture, is introduced into the reaction mixture. The stream of gas preferably comprises 0.5 to 10% by weight of ozone.

The ozonolysis is complete as soon as the reaction mixture turns blue as a result of excess ozone.

When the reaction is complete, excess ozone is advantageously removed by introducing inert gas, for example by introducing nitrogen.

The ozonide formed is worked-up reductively in accordance with known methods, for example by adding dimethyl sulphide, sulphur dioxide, trimethyl phosphite, thiourea, zinc dust in acetic acid, sodium hydrogen sulphite or by means of catalytic hydrogenation.

The starting compounds of the formula (II) can be prepared by known methods.

For example, in a Mannich reaction, an appropriate ketone can be reacted with formaldehyde and dialkylamine. The resulting Mannich base is then heated, and the dialkylamine cleaves off and the α,β-unsaturated ketone of the formula II is formed.

α,β-Unsaturated ketones of the formula II can also be prepared by aldol addition from the appropriate ketones by reaction with acetaldehyde or paraldehyde.

Likewise, the reaction of ketones with "Gold's reagent" [3-(dimethylamino)-2-azaprop-2-en-1-ylidene]dimethylammonium chloride leads to α,β-unsaturated ketones.

The examples below illustrate the process without representing a limitation.

All yields were determined by GC analysis of the reaction mixture, and where the yields are given in percentages, these are mole percentages.

EXAMPLE 1

Preparation of pentane-2,3-dione
(Starting from II, $R^1$=methyl, $R^2$=ethyl, $R^3$=$R^4$=H)

A solution of 88% of 2-methylpent-1-en-3-one (11.36 g; 0.102 mol) in methanol (100 ml) was cooled to −78° C. and ozone was introduced at a rate of 3.4 g/h over 2 h. Excess ozone was then driven out with nitrogen. The reaction mixture was treated with dimethyl sulphide (7.59 g; 0.122 mol) and slowly heated to 25° C. Some of the reaction mixture was distilled off under reduced pressure (240 mbar). The residue obtained was 19.81 g of crude product which comprised 10% by weight of pentane-2,3-dione. This corresponds to a yield of 20% of pentane-2,3-dione in the residue. The distillate (66.93 g) comprised 3% by weight of pentane-2,3-dione, corresponding to a yield of a further 20% of pentane-2,3-dione.

$^1$H NMR (400 MHz, CDCl$_3$)δ=2.78 (q, J=8 Hz, 2H); 2.34 (s, 3H); 1.09 (t, J=8 Hz, 3H)

EXAMPLE 2

Preparation of pentane-2,3-dione
Starting from II, $R^1$=methyl, $R^2$=ethyl, $R^3$=methyl, $R^4$=H A solution of 89% of 4-methylhex-4-en-3-one (11.25 g; 0.089 mol) in methanol (100 ml) was cooled to −78° C. and ozone was introduced at a rate of 3.4 g/h over 5 h. Excess ozone was driven out with nitrogen. The reaction mixture was treated with dimethyl sulphide (6.64 g; 0.107 mol) and slowly heated to 25° C. Some of the reaction mixture was distilled off under reduced pressure (240 mbar). The residue obtained was 20.58 g of crude product, which comprised 10% by weight of pentane-2,3-dione, corresponding to a yield of 23%. The distillate comprised a further 24% of pentane-2,3-dione, corresponding to an overall yield of 47%.

EXAMPLE 3

Preparation of pentane-2,3-dione

Starting from II, $R^1$=methyl, $R^2$=ethyl, $R^3$=dimethylamino, $R^4$=H

A solution of 78% of 1-(dimethylamino)-2-methylpent-1-en-3-one (3.75 g; 0.021 mol) in methanol (35 ml) was cooled to −78° C. and ozone was introduced at a rate of 3.4 g/h over 1 h. Excess ozone was driven out with nitrogen. The reaction mixture was treated with dimethyl sulphide (1.51 g; 0.024 mol) and slowly heated to 25° C. The yield of pentane-2,3-dione was determined as 19% in the reaction mixture.

EXAMPLE 4

Preparation of 2-methylpent-1-en-3-one

II, $R^1$=methyl, $R^2$=ethyl, $R^3$=$R^4$=H, Mannich reaction a-1) 1-(Dimethylamino)-2-methylpentan-3-one A solution of diethyl ketone (200.00 g; 2.322 mol), dimethylamine hydrochloride (94.68 g; 1.161 mol) and 36% of formalin (96.85 g; 1.161 mol) was adjusted to pH 1.00 with 32% aqueous HCl and refluxed for 15 h. After it had cooled to 25° C., the reaction mixture was treated with diethyl ether (100 ml) and the phases were separated. The aqueous phase was adjusted to pH 12 with 30% NaOH (144 g) with cooling, diluted with water (60 g) and extracted with diethyl ether (3×100 ml). These last-mentioned diethyl ether phases were combined, dried over sodium sulphate and concentrated under reduced pressure. The residue obtained was 144.0 g of product, which comprised 94.6% by weight of 1-(dimethylamino)-2-methylpentan-3-one, corresponding to a yield of 82%.

$^1$H NMR (400 MHz, CDCl$_3$) δ=2.80–2.70 (m, 1H); 2.63–2.56 (m, 1H); 2.54–2.47 (m, 2H); 2.19 (s, 6H, —N(CH$_3$)$_2$); 2.17–2.11 (m, 1H); 1.07–1.01 (m, 6H, 2×CH$_3$).

a-2) 2-Methylpent-1-en-3-one

HCl gas (47.4 g; 1.317 mol) was introduced at 25° C. over the course of 2 h into a solution of 1-(dimethylamino)-2-methylpentan-3-one (143.08 g; 1.000 mol) in diethyl ether (1.0 l). The resulting solid was filtered off, washed with diethyl ether (2×500 ml) and dried at 30° C. under reduced pressure (30 mbar). This gave 169.72 g (100%) of 1-(dimethylamino)-2-methylpentan-3-one hydrochloride.

1-(Dimethylamino)-2-methylpentan-3-one hydrochloride (20.00 g; 0.112 mol) was heated to 170–200° C. and the resulting 2-methylpent-1-en-3-one was distilled. This gave 7.29 g of product, which comprised 88% by weight of 2-methylpent-1-en-3-one. The remaining 12% by weight was diethyl ketone.

This corresponds to a yield of 58% of 2-methylpent-1-en-3-one.

$^1$H NMR (400 MHz, CDCl$_3$) δ=5.95 and 5.74 (2×s, 2×1H, C=C$\underline{H}_2$); 2.70 (q, J=8 Hz, 2H, C$\underline{H}_2$CH$_3$); 1.86 (s, 3H, C$\underline{H}_3$); 1.10 (t, J=8 Hz, 3H, CH$_2$C$\underline{H}_3$).

b) 2-Methylpent-1-en-3-one

A solution of diethyl ketone (100.00 g, 1.1610 mol), dimethylamine hydrochloride (47.34 g; 0.5805 mol) and 36% of formalin (48.42 g; 0.5805 mol) was adjusted to pH 1.00 with 1 M HCl (1.25 g) and refluxed for 15 h. After it had been cooled to 25° C, the two-phase reaction mixture was separated. The aqueous phase was washed with diethyl ether (2×50 ml) and the water (28.52 g) was distilled off under reduced pressure (120 mbar) at a bath temperature of 90° C. The bottom product was treated with hydroquinone (4.50 g; 0.0499 mol), heated to 160–200° C., and the resulting 2-methylpent-1-en-3-one was distilled. This gave 22.30 g of a product which comprised 84% by weight of 2-methylpent-1-en-3-one (corresponding to a yield of 33% of 2-methylpent-1-en-3-one) and 13.81 g of a product with 86% by weight of 2-methylpent-1-en-3-one (corresponding to a further 21% yield).

EXAMPLE 5

Preparation of 4-methylhex-4-en-3-one

II, $R^1$=methyl, $R^2$=ethyl, $R^3$=methyl, $R^4$=H, aldol addition

Paraldehyde (51.14 g; 0.387 mol) was added dropwise over 5 h to a solution of diethyl ketone (200.00 g; 2.322 mol) and 98% H$_2$SO$_4$ (17.08 g; 0.1742 mol) at 55° C. The reaction mixture was stirred at 55° C. for 16 h, cooled to 30° C., treated with water (24.0 g) and adjusted to pH=7 with 30% NaOH. The phases were separated and the organic phase was concentrated under reduced pressure. This gave 107.42 g of product, which comprised 77% by weight of 4-methylhex-4-en-3-one (corresponding to a yield of 64%).

$^1$H NMR (400 MHz, CDCl$_3$) δ=6.73 (q, J=8 Hz, 1H); 2.66 (q, J=8 Hz, 2H); 1.85 (d, J=8 Hz, 3H); 1.78 (s, 3H); 1.09 (t, J=8 Hz, 3H).

EXAMPLE 6

Preparation of 1-(dimethylamino)-2-methylpent-1-en-3-one

II, $R^1$=methyl, $R^2$=ethyl, $R^3$=dimethylamino, $R^4$=H, Gold's reagent a-1) Preparation of [3-(dimethylamino)-2-azaprop-2-en-1-ylidene]dimethylammonium chloride A solution of cyanuric chloride (70.0 g; 0.379 mol) and N,N-dimethylformamide (183.14 g; 2.510 mol) in 1,4-dioxane (380 ml) was stirred under N$_2$ for 10 h at 65° C. The reaction mixture was cooled to 20° C. The resulting solid was filtered off and dried at 50° C. under reduced pressure (30 mbar) over phosphorus pent-oxide. This gave 149.29 g (80%) of [3-(dimethylamino)-2-azaprop-2-en-1-ylidene]dimethylammonium chloride.

$^1$H NMR (400 MHz, CDCl$_3$) δ=9.60 (s, 2H); 3.43 (s, 3H); 3.25 (s, 3H).

IR (KBr) 3453(m), 3401(m), 1613(s), 1502(w), 1418(m), 1345(s), 1126(m) cm$^{-1}$.

a-2) 1-(Dimethylamino)-2-methylpent-1-en-3-one

Diethyl ketone (29.71 g; 0.345 mol) and [3-(dimethylamino)-2-azaprop-2-en-1-ylidene]dimethylammonium chloride (37.64 g; 0.230 mol) were added to a solution of 30% of sodium methoxide in methanol (41.41 g; 0.230 mol) and methanol (305 ml) at 20° C. under N$_2$. The reaction mixture was refluxed for 18 h and then concentrated under reduced pressure. The residue was dissolved in dichloromethane (300 ml) and washed with saturated sodium bisulphite solution (3×100 ml). The organic phase was dried over Na$_2$SO$_4$ and concentrated under reduced pressure. This gave 26.60 g of product, which comprised 42% by weight of 1-(dimethylamino)-2-methylpent-1-en-3-one (corresponding to a yield of 34%).

$^1$H NMR (400 MHz, CDCl$_3$) δ=7.20 (s, 1H); 3.07 (s, 6H); 2.45 (q, J=8 Hz, 2H); 1.96 (s, 3H); 1.10 (t, J=8 Hz, 3H).

What is claimed is:

1. A process for preparation of an α-dicarbonyl compound of formula:

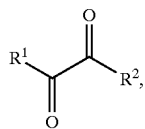

in which $R^1$ and $R^2$, independently of one another, are $C_{1-6}$-alkyl, comprising reacting an α,β-unsaturated ketone of formula:

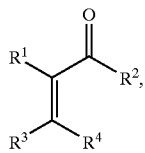

in which $R^1$ and $R^2$ have the meaning given above, and $R^3$ and $R^4$, independently of one another, are hydrogen, $C_{1-6}$-alkyl or di-$C_{1-6}$-alkylamino, with ozone, in the absence of a catalyst and working up reductively ozonide formed in reaction step.

2. The process according to claim 1, in which $R^1$ is methyl and $R^2$ is ethyl.

3. The process according to claim 2, wherein an ozone-containing stream of gas is passed into the reaction mixture at a temperature of from −100 to +30° C.

4. The process according to claim 1, wherein an ozone-containing stream of gas is passed into the reaction mixture at a temperature of from −100 to +30° C.

* * * * *